United States Patent [19]
Subramaniam

[11] Patent Number: 5,643,580
[45] Date of Patent: Jul. 1, 1997

[54] BIOCOMPATIBLE COATING, MEDICAL DEVICE USING THE SAME AND METHODS

[75] Inventor: Raj Subramaniam, Fremont, Calif.

[73] Assignee: Surface Genesis, Inc., Sunnyvale, Calif.

[21] Appl. No.: 324,413

[22] Filed: Oct. 17, 1994

[51] Int. Cl.$^6$ ............................. A61K 41/00; B05D 3/06
[52] U.S. Cl. ................... 424/400; 427/2.12; 427/2.13; 427/2.28; 427/2.3; 427/535
[58] Field of Search ................... 424/400; 623/11, 623/1, 66; 427/2, 2.12, 2.13, 2.28, 2.3, 535; 436/501

[56] References Cited

U.S. PATENT DOCUMENTS

| | | | |
|---|---|---|---|
| 4,973,493 | 11/1990 | Guire | 623/901 |
| 4,979,959 | 12/1990 | Guire | 623/66 |
| 5,002,582 | 3/1991 | Guire et al. | 623/901 |
| 5,217,492 | 6/1993 | Guire et al. | 623/66 |
| 5,258,041 | 11/1993 | Guire et al. | 427/2.13 |
| 5,263,992 | 11/1993 | Guire | 623/66 |
| 5,324,647 | 6/1994 | Rubens et al. | 436/8 |

Primary Examiner—Thurman K. Page
Attorney, Agent, or Firm—Flehr, Hohbach, Test, Albritton & Herbert

[57] ABSTRACT

The invention involves using a plasma to functionalize a surface of medical devices such as catheters, particularly intracardial catheters, with covalently bound thermochemically reactive groups. The surface is further contacted with a bioactive agent, particularly antithrombogenic coatings, which is thermochemically covalently coupled to the reactive group to form a therapeutically effective coating. The selected bioactive agent is then covalently bound to the surface by thermochemical reaction with the surface reactive groups. In another embodiment, the functionalizing step comprises contacting the surface with a Langmuir-Blodgett film comprising an amphipathic compound and a bioactive agent and using a plasma to covalently crosslink the Langmuir-Blodgett film to the medical device surface and to the bioactive agent. Medical devices prepared by the subject methods are also provided.

22 Claims, 6 Drawing Sheets

STENT

BIOCOMPATIBLE COATING, MEDICAL DEVICE USING THE SAME AND METHODS

The Field of the invention is biocompatible coatings of medicals devices, particularly antithrombogenic coatings for intravascular catheters.

Medical devices which have direct contact with blood flow have a tendency to promote localized thrombosis. Additionally, it is often desirable to promote localized thrombosis at the sites of wounds. The present invention provides novel methods for applying therapeutic coatings such as thrombogenic and antithrombogenic coatings to a variety of medical devices.

SUMMARY OF THE INVENTION

The invention provides covalently attached therapeutic coatings for surfaces of medical devices and a variety of methods for making medical devices with such coatings.

In one embodiment, the methods involve functionalizing a surface of the medical device with covalently bound thermochemically reactive groups. The surface is further contacted with a bioactive agent which is thermochemically covalently coupled to the reactive group to form a therapeutically effective coating. In a preferred embodiment, the functionalizing step comprises contacting the surface with a plasma to form the thermochemically reactive groups. A wide variety of reactive groups which provide convenient reactants for the selected bioactive agent may be used. The selected bioactive agent is then covalently bound to the surface by thermochemical reaction with the surface reactive groups.

In another embodiment, the functionalizing step comprises contacting the surface with a Langmuir-Blodgett film comprising an amphipathic compound and a bioactive agent. A plasma or thermochemical means are then used to covalently crosslink the Langmuir-Blodgett film to the medical device surface and to the bioactive agent. Optionally, in this embodiment, the surface may also be functionalizing with a first thermochemically reactive group capable of reacting with at least one of the amphipathic compound and the bioactive agent. Similarly, the bioactive agent may be derivatized with a second reactive group capable of reacting with the first reactive group.

In these methods, the bioactive agent is advantageously derivatized with a label capable of providing a detectable signal. Hence the detectable signal is used to quantify the bound bioactive agent on the device's surface.

Where the bioactive agent is antithrombogenic, it may be a relatively irreversible thrombin inhibitor, such as D-Phe-Pro-Arg-chloromethyl ketone, or a relatively reversible thrombin inhibitor, such as heparin or a polypeptide comprising the amino acid sequence Ile-Pro-Glu-Glu-Tyr-Leu-Gln.

Exemplary medical devices for antithrombogenic coatings include catheters, particularly intracardial catheters, vasculature stents and grafts and various blood transfer devices such as blood oxygenators, dialysis and plasmapheresis devices, etc. Exemplary medical devises for thrombogenic coatings include wound closing and wound covering devises such as sutures, bandages, etc.

The medical devices of the invention have a surface with a covalently attached dry therapeutic coatings. In one embodiment, the coating comprises thermochemically reactive groups covalently bound to the surface and a bioactive agent covalently bound to a portion but fewer than all of the thermochemically reactive groups. In another embodiment, the coating comprises a Langmuir-Blodgett film comprising an amphipathic compound and a bioactive agent, where the amphipathic compound is covalently crosslinked to the surface, and the bioactive agent is covalently crosslinked to the amphipathic compound.

The invention also provides general methods for treating a surface of a medical device with a therapeutic covalent coating of a bioactive agent; thereafter, washing the surface to remove any bioactive agent which is not covalently bound; thereafter, causing a reagent capable of selectively, non-covalently binding to the bioactive agent to become selectively and noncovalently bound to the bioactive agent; thereafter, washing the surface to remove any of such reagent which is not selectively bound to the bioactive agent; thereafter, detecting a radiative signal at an intensity which meets or exceeds a predetermined intensity which correlates with the presence of coating of a predetermined amount of the bioactive agent covalently bound to the surface. For example, the reagent may be a specific antibody and the signal fluorescence.

BRIEF DESCRIPTION OF THE DRAWINGS

FIG. 1 shows a typical plasma chamber.

FIG. 2 shows a typical plasma surface modification system.

FIG. 3 shows a catheterized heart.

FIG. 4 shows a typical electrophysiology catheter.

FIG. 5 shows a typical stent.

FIG. 6 shows a typical blood oxygenator.

DETAILED DESCRIPTION OF THE INVENTION

Figure 1:
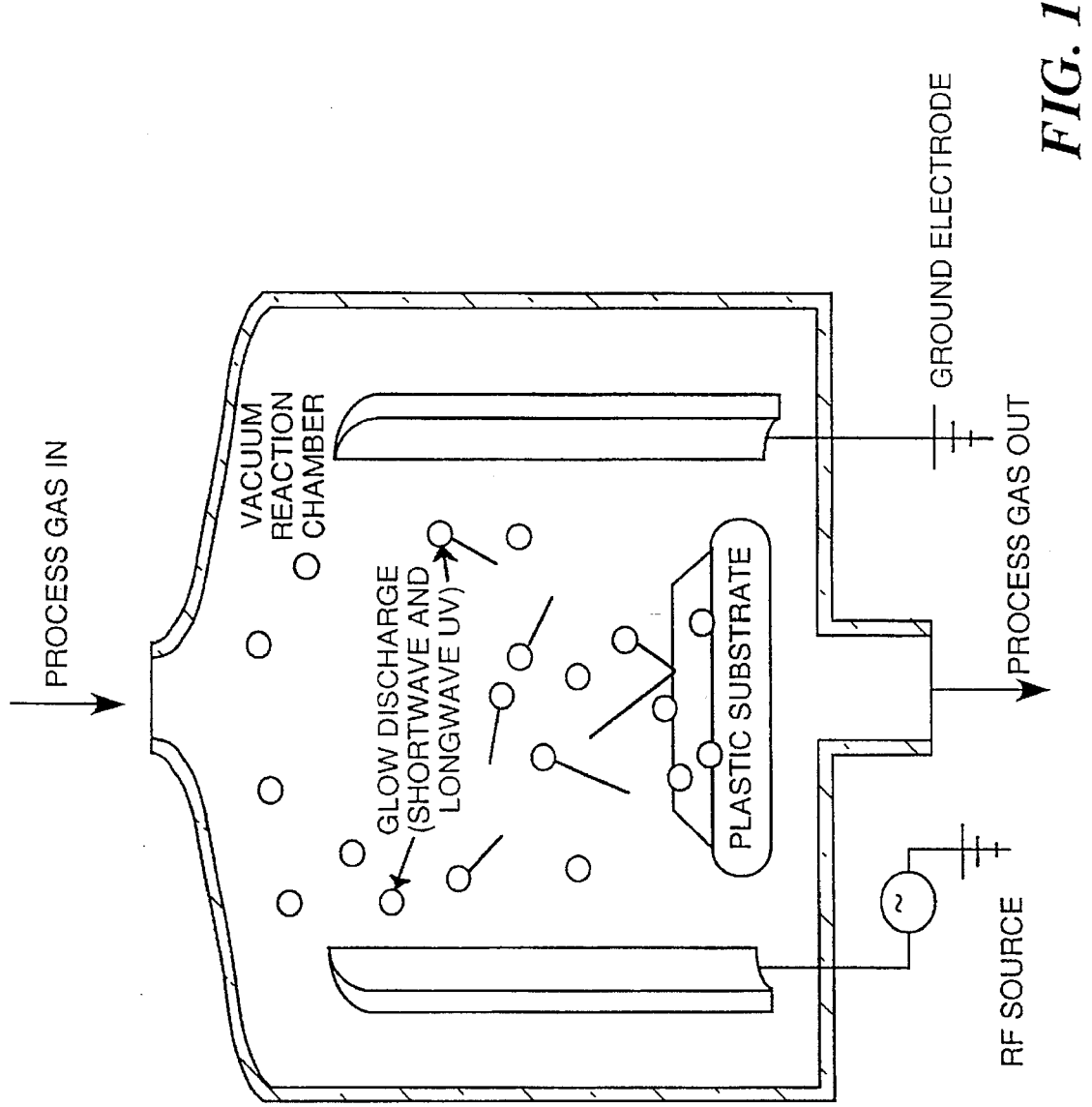
FIG. 1.
Figure 2:
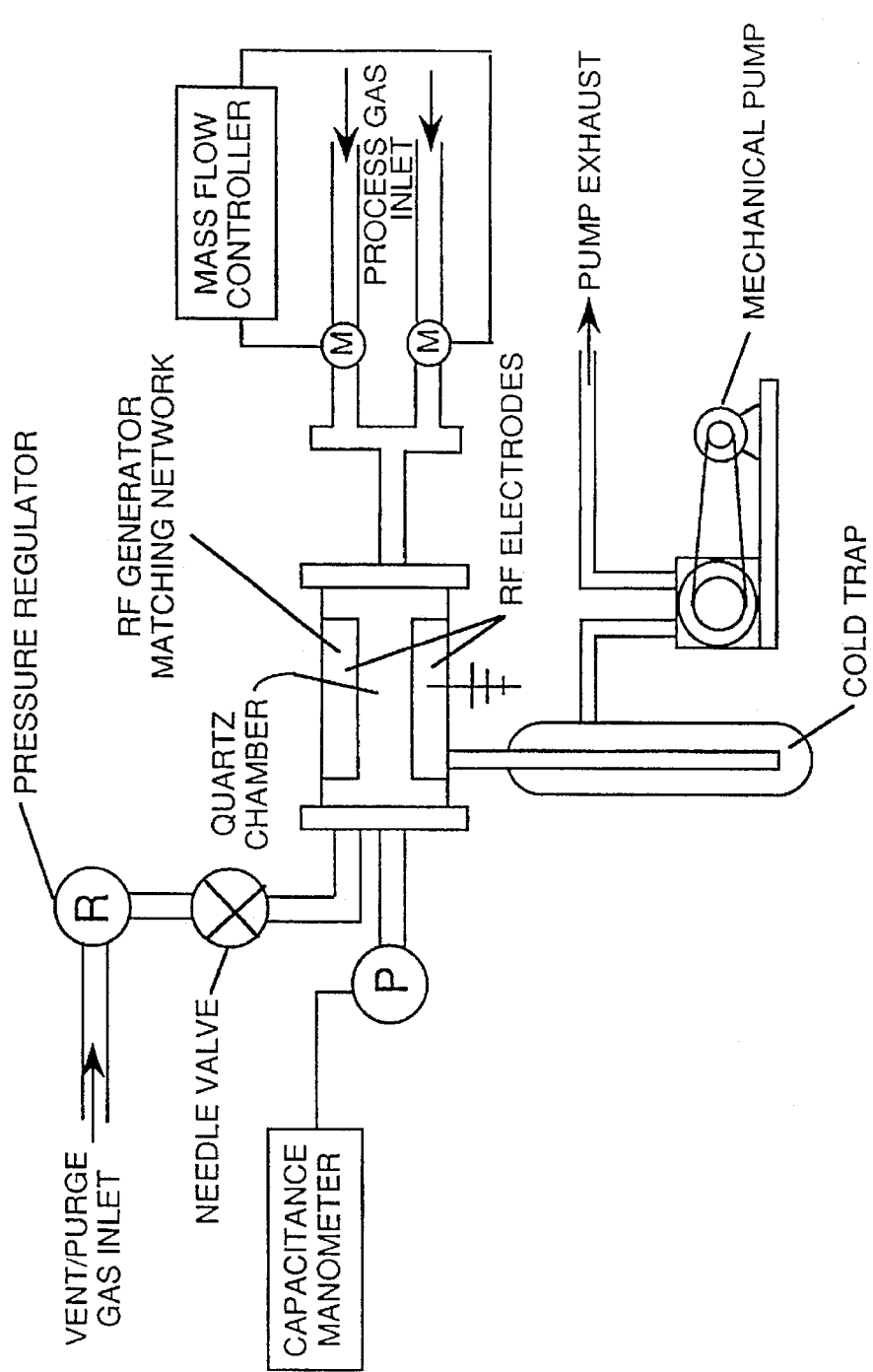
FIG. 2.
Figure 3:
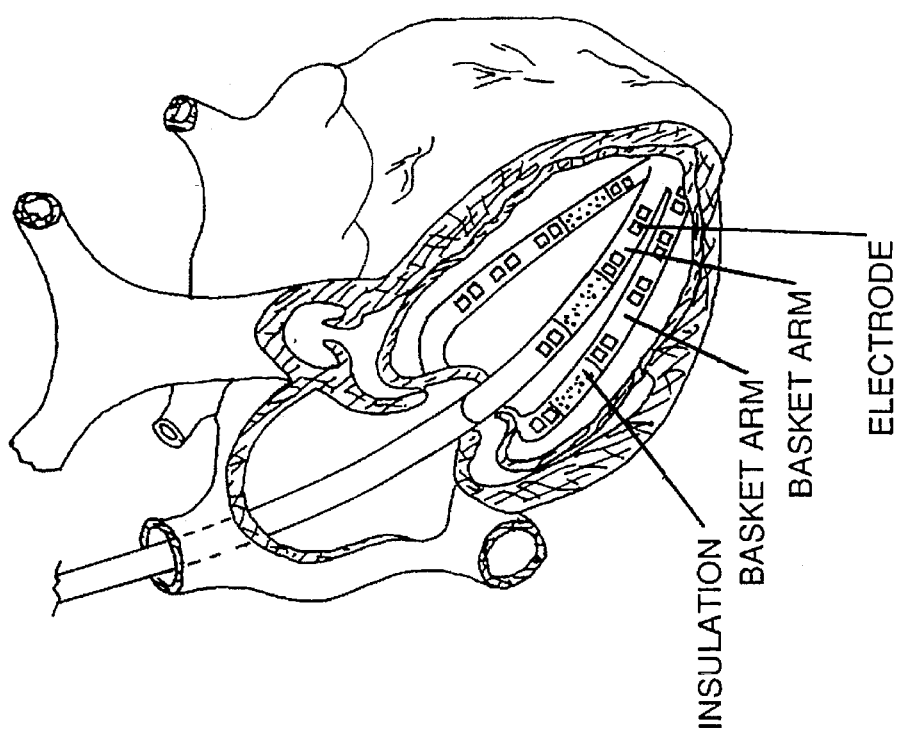
FIG. 3.
Figure 4:
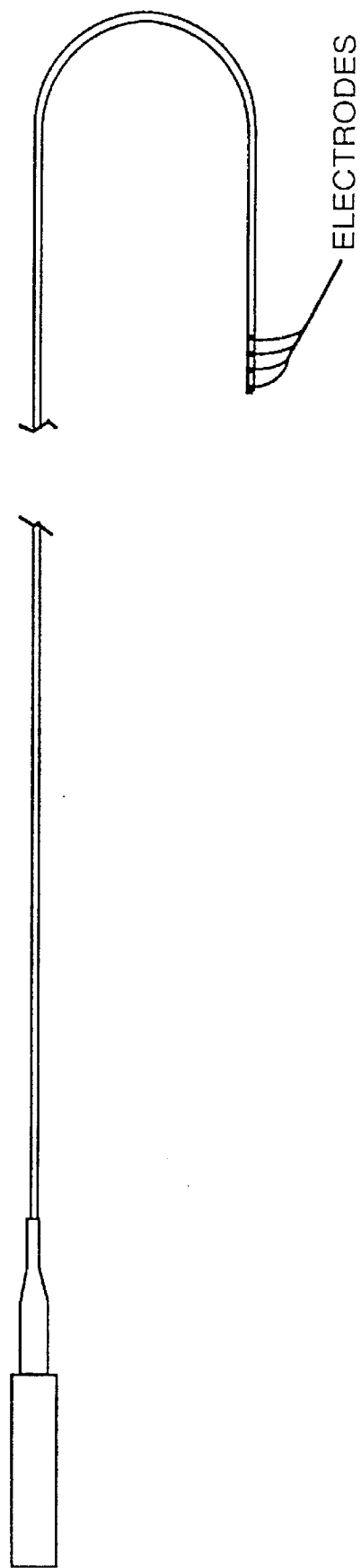
FIG. 4.
Figure 5:
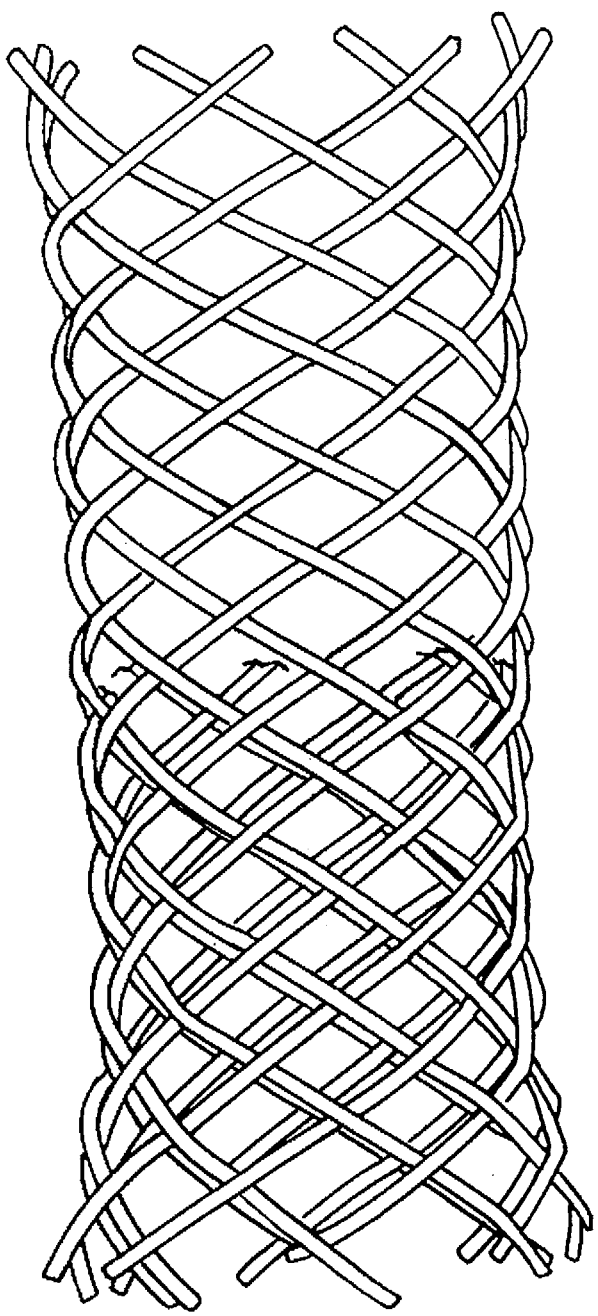
FIG. 5.
Figure 6:
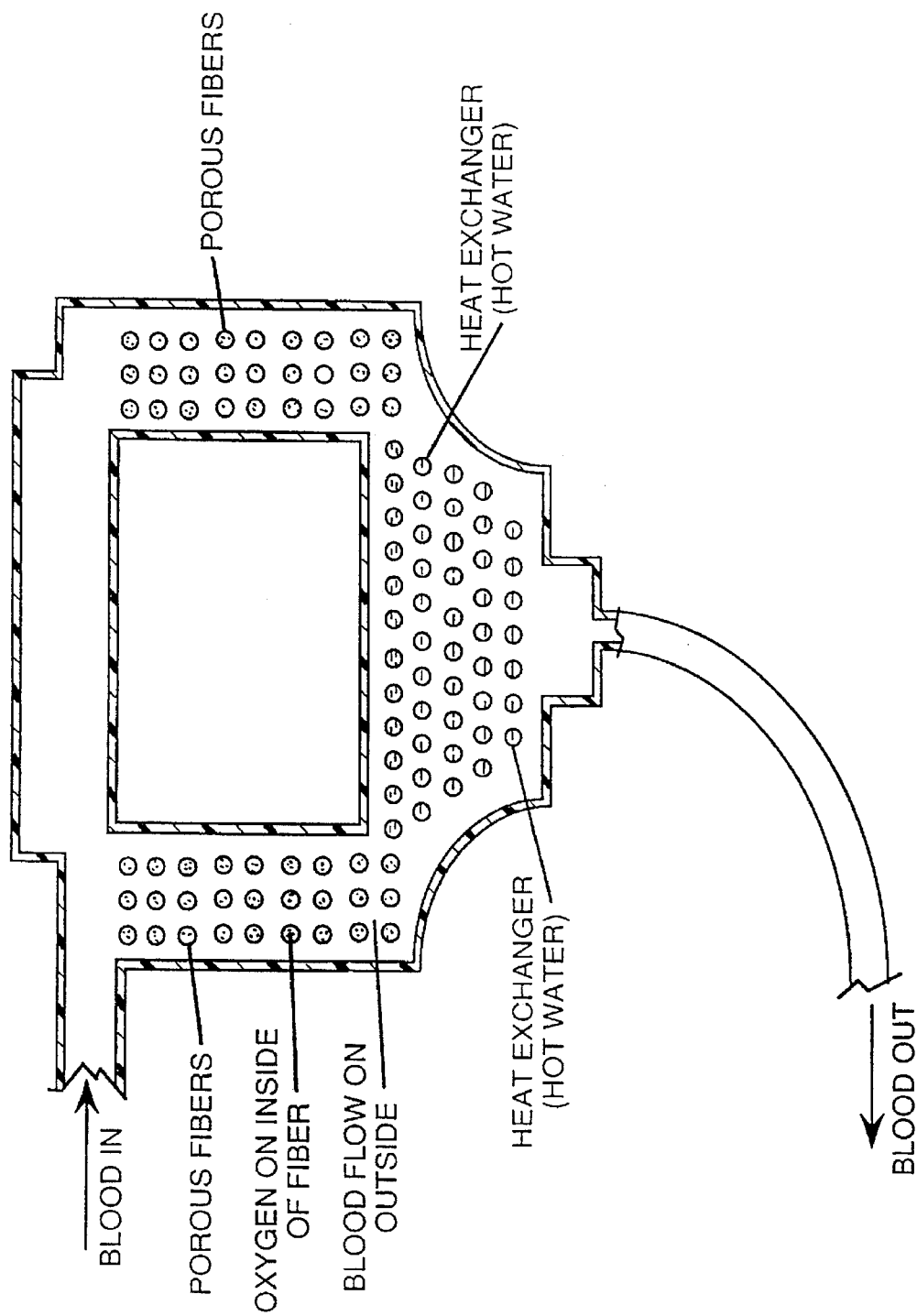
FIG. 6.

The invention provides a wide variety of covalently attached biocompatible coatings for surfaces of medical devices. In particular embodiments, the invention provides covalently attached antithrombogenic coatings for medical devise surfaces exposed to blood flow and thrombogenic coatings for medical devise surfaces not exposed to blood flow continuous with bodily circulation. The invention provides a variety of methods for making medical devices with such coatings.

The methods involve functionalizing the selected surface of a medical device with covalently bound reactive groups. The surface is further contacted with a bioactive agent, in particular an antithrombogenic agent, which is covalently coupled to the reactive group to form a coating effective to inhibit the formation of thrombus when the surface is exposed to blood flow continuous with bodily blood circulation. While described below primarily with antithrombogenic agents, it is understood that a wide variety of bioactive agents, e.g. antibiotics, may be substituted for the antithrombogenic agents, depending on the desired characteristics of the device's surface.

In one embodiment, the functionalizing step comprises contacting the surface with a plasma to form chemically reactive groups. The plasma used in this method are conveniently "low temperature" or "cold" plasma produced by glow discharge. A low temperature plasma is created in evacuated chamber refilled with a low pressure gas. The pressures are typically in the order of 0.1 to 10 torr and the gas is excited by electrical energy in the radio frequency range (RF). The glow discharge, typically in the range of 100 to 1,000 watts, depending on the chamber volume, contains ions, electrons, metastables, and photons. When these species interact with the surface a variety of reactions can take place. Bonds can be broken, new bonds are formed, and if a reactive gas is used this can also react with the substrate.

A wide variety of reactive groups which provide convenient reactants for the selected bioactive agent may be used. For example, hydroxyl groups are attached to the surface either with use of methane/oxygen plasma or water/oxygen plasma. A carboxyl rich surface are generated by the deposition of acrylic acid to the surface of the device. Frequently, the reactant is provided with a carrier gas; for example, methane gas which additionally provides surface polyalkyl (hydrocarbon) chains may be advantageously used where otherwise unreactive metal surfaces are to be coated. Alternatively, an inert cattier gas such as helium or argon may be used. Typically the gas/reactant are introduced in a ratio of approximately 3:1.

Device surfaces are typically treated for from about 0.5 to about 30 minutes, desirably obtaining a uniform distribution of amine on the plastic surface. The water surface tension of the modification may be confirmed by the water contact angle measurements.

The selected bioactive agent is covalently bound to the surface by thermochemical reaction with the surface reactive groups. For example, carboxyl groups readily react with xylose moieties on heparin in the presence of 1-ethyl-3-(-dimethylaminopropyl)carbodiminde, EDC, to form an ester linkage. Hirudin and its analogs are conveniently bound to carboxyl rich surface by introduction of specifically engineered amino group at the carboxyl terminus of the peptide away from the active amino terminus.

In another embodiment, the functionalizing step comprises contacting the surface with a Langmuir-Blodgett film comprising an amphipathic compound and a bioactive agent. A crosslinking agent is then used to covalently crosslink the Langmuir-Blodgett film to the medical device surface and to the bioactive agent. For example, an argon or helium plasma chamber is used to contact the Langmuir-Blodgett film-coated surface with high energy photons and electrons capable of chemically crosslinking the amphipathic compound and the bioactive agent. The amphipathic compound and bioactive agent may be applied sequentially or simultaneously. Similarly, the surface-amphipathic compound crosslinking and amphipathic compound-bioactive agent crosslinking may be performed either sequentially or simultaneously. Optionally, in this embodiment, the surface may also be functionalizing with a first reactive group capable of reacting with at least one of the amphipathic compound and the bioactive agent. Similarly, the bioactive agent may be derivatized with a second reactive group capable of reacting with the first reactive group.

In these methods, the bioactive agent is advantageously derivatized with a label, particularly a fluorescent or colorimetric label, capable of providing a detectable signal. Hence the detectable signal is used to quantify the bound bioactive agent on the device's surface. Where an antithrombogenic agent is used, it may be a relatively irreversible thrombin inhibitor, such as D-Phe-Pro-Arg-chloromethyl ketone, or a relatively reversible thrombin inhibitor, such as heparin or a polypeptide comprising the amino acid sequence Ile-Pro-Glu-Glu-Tyr-Leu-Gln. Prothrombogenic agents include thromboplastin, thrombocytin, and other clotting factors. Other useful bioactive agents include antimicrobial and antifungal agents, growth factors, etc.

For antithrombogenic coatings, the medical device has a surface destined for contact with blood flow continuous with bodily blood circulation as distinguished from blood permanently removed from bodily circulation. Exemplary devices include catheters, particularly intracardial catheters, vasculatur stents and grafts and various blood transfer devices such as blood oxygenators, dialysis and plasmapheresis devices, etc. In a specific embodiment, the medical device is an intracardial a catheter probe for introduction into a chamber of the heart, having proximal and distal extremities and comprising a flexible elongate tubular member having at least one lumen extending therethrough extending the length thereof and having a distal extremity, a plurality of longitudinally and radially spaced apart electrodes, expandable means secured to the distal portion of said flexible elongate tubular member and being movable between a contracted position and an expanded position, means mounting said electrodes on said expandable means whereby when said expandable means is moved to the expanded position in the chamber of the heart the electrodes are moved into engagement with the wail forming the chamber of the heart, means coupled to the expandable means for moving said expandable between said contracted and expanded positions, said expandable means including a plurality of plastic elements having surfaces exposed to the blood and said elements having spaces therebetween when in the expanded position through which the blood can flow, lead means for conducting electrical energy in contact with the electrodes and extending into said flexible elongate tubular member and electrical means connected to said lead means for performing electrical functions with respect to said electrodes.

Medical devices suitable for thrombogenic coatings include devices for occluding aneurisms or ruptured vessels, for closure of percutaneous or vascular puncture sites, etc. For example, the proximal end of the introducer of such devices as laproscopes, catheters, etc. may also be advantageously so coated.

Many of the subject medical devices of the invention have a blood flow-contacting surface with a covalently attached dry coating to inhibit thrombosis. In one embodiment, the coating comprises reactive linking groups covalently bound to the surface and a bioactive agent covalently bound to a portion but fewer than ail of the reactive linking groups. In another embodiment, the coating comprises a Langmuir-Blodgett film comprising an amphipathic compound and a bioactive agent, where the amphipathic compound is covalently crosslinked to the surface, and the bioactive agent is covalently crosslinked to the amphipathic compound.

The invention also provides general methods for treating a surface of a medical device to inhibit thrombosis which involve causing a bioactive agent to become covalently bound to a medical device surface exposed to blood flow continuous with bodily blood circulation; thereafter, washing the surface to remove any bioactive agent which is not covalently bound; thereafter, causing a reagent capable of selectively, non-covalently binding to the bioactive agent to become selectively and noncovalently bound to the bioactive agent; thereafter, washing the surface to remove any of such reagent which is not selectively bound to the bioactive agent; thereafter, detecting a radiative signal at an intensity which meets or exceeds a predetermined intensity which correlates with the presence of coating of a predetermined amount of the bioactive agent covalently bound to the surface. For example, the reagent may be a specific antibody and the signal fluorescence.

EXAMPLES

In a specific case, an antithrombogenic coating was applied to the surface of an electrophysiology catheter by this method. The catheter was made of PBax tubing loaded with barium salt. The distal end of catheter had annular platinum electrodes and a platinum cap. First the catheter was placed in the plasma chamber and evacuated. A mixture of methane (490 SCCM) and ammonia (161 SCCM) were introduce into the chamber maintained at 0.265 torr pressure. A 400 watts glow discharge established between the electrodes. The sample was treated for 3 minutes under the conditions. Under these condition there uniform distribution of amine on the plastic surface. Between 40 to 100 % of the surface is covered by amine groups. The modification was confirmed by the water contact angle measurements. The contact angle was 85 degrees for the untreated sample and the treated sample had contact angle of 41 degrees.

The bioactive agent was derivatized when necessary to improve the covalent binding to the device. In case of heparin the xylose can be reacted with the carboxyl group on the plasma treated surface by simple esterification in the presence of 1-ethyl-3-(3-dimethylaminopropyl)carbodimide (EDC). 200 mg of EDC was dissolved in the 5 ml of water and pH was adjusted to 4 with dilute hydrochloric acid. The device was immersed in this solution. Heparin (200,000 units) dissolved in 5 ml of water was added to this. The pH was adjusted to 4 again. The solution was periodically stirred for two hour at room temperature. An additional 100 mg of EDC was added and the reaction continued for 12 hr. The device was then washed with phosphate buffered saline to remove unreacted heparin. The device was then air dried and stored moisture free.

The effectiveness of the coating was determined by in-vitro by blood clotting time. Citrated cow blood was incubated at 37 ° C. A heparin coated device was immersed in the blood. The clotting was initiated by the addition of 2-3 drops of 10% calcium chloride solution. Control tubes with no device and an uncoated device were also maintained. The time for clot formation was determined by examining the test tube periodically. In the control tests tube the clotting started in less then 15 minutes. Heparin coated devices prevented the clotting at least for 2 hr.

In vivo, studies were conducted in sheep. The coated device was introduced to left ventricle. After leaving the device in place for one hour the device was withdrawn. The device was gentle rinsed in saline and the surface was examined for thrombus. With the Heparin coating very little or no thrombus formation was observed.

The stability of coating was determined by extracting the device in saline for 1 to 24 hr. at 37° C. and then performing the in vitro studies described above. There was no substantial difference in the clotting times for the saline extracted devices. Nearly all the heparin is covalently bound to the device.

In another example, in a Langmuir-Blodgett trough, a laminar flow of water at 1 gallon/hr was established. At one end of the trough a dispenser a solution of an amphiphilic molecules in a water miscible solvent such as acetone is dispensed at controlled rate. The amphiphilic molecules will spread on the surface of the water and form a film. If they are rod like molecule they tend align within this film. By controlling dispensing rate of the amphiphile the thickness or the number mono layer in the film can be controlled. When a device such as a catheter is immersed in the water and slowly withdrawn the film is transferred to the device surface. The film thus transferred can be dried on surface to give a highly oriented coating. Additional layers of the coating can be applied by repeated dipping and drying. A multilayer coating can be annealed to get interpenetration of the layers. LB film are not generally very stable. If a device coated with LB film is subjected plasma treatment covalent bond can be generated between the rods and between the device and the film. Such a crosslinked coating is very robust. To a LB trough with laminar water flow a solution of gamma-methyl-L-glutamate-gamma-n-octadecyl-L-glutamate coplyomer dispensed through an arrow slot just touching the water surface. The rate was controlled to attain a double layer of glutamtae polymer. The film was transferred to a intercardial catheter made of polyethylene and gold sensing elements. The film was air dried at 45° C. for 1 hr. This was then coated for a second time with a layer of himdin derivatized at the carboxyl terminus with octadecyl-L-glutamate. The second bioactive layer was air dried as before. Then this device was placed in a plasma chamber and subjected to an argon glow discharge for 3 min. at 300 watt. The high energy particle induce high reactive free radicals with in the LB film. These radical then covalently link the aligned film components as well as the film to the substrate. Poly(tetramethoxytertraoctoxyphthalocyainato) polysiloxane, isopentyl cellulose and butylcellulose are other examples of materials that are hairy rods that form nice LB films. A variety of bioactive peptides can be derivatized to form self assembled films.

The device can be functionalized first with plasma to have reactive function such as carboxyl, hydroxyl, carbonyl or amine group before LB film deposition. This then can be subjected a procedure as described above.

The LB film layer can also be formed by a mixture of the rod-like amphipiles and the derivatized biomolecule in a single dip process. This will give a coating of amphiphiles interspersed with bioactive moieties. This then can be covalently linked using inert gas plasma.

What is claimed is:

1. A method for treating a surface of a medical device to inhibit thrombosis comprising steps:

functionalizing a surface of a medical device by contacting said surface with a low temperature plasma which surface is exposed to blood flow continuous with bodily blood circulation with a first reactive group, contacting said surface with an antithrombogenic agent capable of reacting with said first reactive group, and causing said antithrombogenic agent to react with said first reactive group to covalently bind said antithrombogenic agent to said surface to form a coating on said surface which coating is effective to inhibit the formation of thrombus when said surface is exposed to blood flow continuous with bodily blood circulation.

2. A method for treating a surface of a medical device to inhibit thrombosis comprising steps:

contacting a surface of a medical device which surface is exposed to blood flow continuous with bodily blood circulation with a Langmuir-Blodgett film comprising an amphipathic compound;

contacting said surface with an antithromobogenic agent;

covalently crosslinking said antithrombogenic agent with said amphipathic compound;

covalently crosslinking said amphipathic compound to said surface;

to form a coating on said surface which coating is effective to inhibit the formation of thrombus when said surface is exposed to blood flow continuous with bodily blood circulation;

wherein at least one of said crosslinking steps comprises contacting said surface with a low temperature plasma.

3. A method according to claim 1 wherein said contacting step comprises contacting said surface with an antithrombogenic agent derivatized with a second reactive group capable of reacting with said first reactive group to covalently bind said antithrombogenic agent to said surface.

4. A method according to claim 1, wherein said contacting step comprises contacting said surface with an antithrombogenic derivatized with a label, wherein said label is capable of providing a detectable signal.

5. A method according to claim 1, wherein said contacting step comprises contacting said surface with an irreversible thrombin inhibitor.

6. A method according to claim 1, wherein said contacting step comprises contacting said surface with an reversible thrombin inhibitor.

7. A method according to claim 1, wherein said contacting step comprises contacting said surface with D-Phe-Pro-Arg-chloromethyl ketone.

8. A method according to claim 1 wherein said contacting step comprises contacting said surface with heparin.

9. A method according to claim 1 wherein said contacting step comprises contacting said surface with a polypeptide comprising the amino acid sequence Ile-Pro-Glu-Glu-Tyr-Leu-Gln.

10. A method according to claim 1 wherein said functionalizing step comprises functionalizing a surface of a catheter, stent, graft, or blood transfer device.

11. A method according to claim 1 for treating a surface of an intracardial catheter probe which is exposed to blood within a body to inhibit formation of thrombus, wherein said catheter probe is for introduction into a chamber of the heart, has proximal and distal extremities and comprises a flexible elongate tubular member having at least one lumen extending therethrough extending the length thereof and having a distal extremity, a plurality of longitudinally and radially spaced apart electrodes, expandable means secured to the distal portion of said flexible elongate tubular member and being movable between a contracted position and an expanded position, means mounting said electrodes on said expandable means whereby when said expandable means is moved to the expanded position in the chamber of the heart the electrodes are moved into engagement with the wall forming the chamber of the heart, means coupled to the expandable means for moving said expandable between said contracted and expanded positions, said expandable means including a plurality of plastic elements having surfaces exposed to the blood and said elements having spaces therebetween when in the expanded position through which the blood can flow, lead means for conducting electrical energy in contact with the electrodes and extending into said flexible elongate tubular member and electrical means connected to said lead means for performing electrical functions with respect to said electrodes, said method comprising steps: functionalizing a surface of said intracardial medical device with a first reactive group, contacting said surface with an antithrombogenic agent capable of reacting with said first reactive group, and causing said antithrombogenic agent to react with said first reactive group to covalently bind said antithrombogenic agent to said surface to form a coating on said surface which is effective to inhibit the formation of thrombus when said surface is exposed to blood within a body.

12. A method according to claim 2, wherein said coating steps are performed simultaneously.

13. A method according to claim 2, wherein said crosslinking steps are performed simultaneously.

14. A method according to claim 2, further comprising prior to said coating said surface with a Langmuir-Blodgett film:

functionalizing said surface with a first reactive group capable of reacting with at least one of said amphipathic compound and said antithrombogenic agent.

15. A method according to claim 14 wherein said antithrombogenic agent is derivatized with a second reactive group capable of reacting with said first reactive group.

16. A method according to claim 1, wherein contacting said surface with an antithrombogenic agent comprises contacting said surface with an antithrombogenic derivatized with a label, wherein said label is capable of providing a detectable signal.

17. A method for treating a surface of a medical device to inhibit thrombosis comprising steps:

contacting an antithrombogenic agent with a surface of a medical device which surface is exposed to blood flow continuous with bodily blood circulation; thereafter causing said antithrombogenic agent to become covalently bound to said surface using a low temperature plasma; thereafter, washing said surface to remove from said surface any of said antithrombogenic agent which is not covalently bound to said surface; thereafter, contacting said surface with a reagent capable of selectively, non-covalently binding said antithrombogenic agent;

causing said reagent to become selectively and noncovalently bound to said antithrombogenic agent; thereafter, washing said surface to remove from said surface any of said reagent which is not selectively bound to said antithrombogenic agent; thereafter, detecting a radiative signal at an intensity which meets or exceeds a predetermined intensity, wherein a radiative signal at said predetermined intensity correlates with the presence of coating of a predetermined amount of said antithrombogenic agent covalently bound to said surface, said coating being effective to inhibit the formation of thrombus when said surface is exposed to blood flow continuous with bodily blood circulation.

18. A method according to claim 17, wherein said reagent is an antibody and said radiative signal is fluorescence.

19. A method for treating a surface of a medical device to provide said surface with a therapeutic coating comprising steps:

functionalizing a surface of a medical device which surface is exposed to blood flow continuous with bodily blood circulation with a first reactive group using a low temperature plasma, contacting said surface with a bioactive agent capable of reacting with said first reactive group, and causing said bioactive agent to react with said first reactive group to covalently bind said bioactive agent to said surface to form a coating on said surface which coating is therapeutic when said surface is exposed to blood flow continuous with bodily blood circulation.

20. A method for treating a surface of a medical device to provide said surface with a therapeutic coating comprising steps:

contacting a surface of a medical device which surface is exposed to blood flow continuous with bodily blood circulation with a Langmuir-Blodgett film comprising an amphipathic compound;

contacting said surface with an antithromobogenic agent;

covalently crosslinking said bioactive agent with said amphipathic compound;

covalently crosslinking said amphipathic compound to said surface;

to form a coating on said surface which coating is effective to inhibit the formation of thrombus when said surface is exposed to blood flow continuous with bodily blood circulation;

wherein at least one of said crosslinking steps comprises contacting said surface with a low temperature plasma.

21. A method for treating a surface of a medical device to provide said surface with a therapeutic coating comprising steps:

contacting an bioactive agent with a surface of a medical device which surface is exposed to blood flow continuous with bodily blood circulation; thereafter causing said bioactive agent to become covalently bound to said surface using a low temperature plasma; thereafter, washing said surface to remove from said surface any of said bioactive agent which is not covalently bound to said surface; thereafter, contacting said surface with a reagent capable of selectively, non-covalently binding said bioactive agent;

causing said reagent to become selectively and noncovalently bound to said bioactive agent; thereafter, washing said surface to remove from said surface any of said reagent which is not selectively bound to said bioactive agent; thereafter, detecting a radiative signal at an intensity which meets or exceeds a predetermined intensity, wherein a radiative signal at said predetermined intensity correlates with the presence of coating of a predetermined amount of said bioactive agent covalently bound to said surface, said coating is therapeutic when said surface is exposed to blood flow continuous with bodily blood circulation.

22. A method for treating a surface of a medical device to promote thrombosis comprising steps:

functionalizing a surface of a medical device by contacting said surface with a low temperature plasma which surface is exposed to blood not in continuous flow with bodily blood circulation with a first reactive group, contacting said surface with an thrombogenic agent capable of reacting with said first reactive group, and causing said thrombogenic agent to react with said first reactive group to covalently bind said thrombogenic agent to said surface to form a coating on said surface which is effective to promote the formation of thrombus when said surface is exposed to blood not in continuous flow with bodily blood circulation.

* * * * *